(12) United States Patent
Kufer et al.

(10) Patent No.: US 7,235,641 B2
(45) Date of Patent: Jun. 26, 2007

(54) BISPECIFIC ANTIBODIES

(75) Inventors: Peter Kufer, Munich (DE); Meera Berry, Munich (DE); Patrick Baeuerle, Munich (DE); Christian Itin, Munich (DE)

(73) Assignee: Micromet AG, Munich (DE)

( * ) Notice: Subject to any disclaimer, the term of this patent is extended or adjusted under 35 U.S.C. 154(b) by 283 days.

(21) Appl. No.: 10/743,697

(22) Filed: Dec. 22, 2003

(65) Prior Publication Data

US 2005/0136050 A1    Jun. 23, 2005

(51) Int. Cl.
C07K 16/18     (2006.01)
C07K 16/28     (2006.01)
G01N 33/53     (2006.01)

(52) U.S. Cl. .............................. 530/387.3; 530/388.22; 436/548

(58) Field of Classification Search ...................... None
See application file for complete search history.

(56) References Cited

U.S. PATENT DOCUMENTS

| | | | |
|---|---|---|---|
| 5,258,498 A | | 11/1993 | Huston et al. |
| 5,489,288 A | * | 2/1996 | Buelna ........................ 606/144 |
| 5,525,491 A | | 6/1996 | Huston et al. |
| 5,658,570 A | * | 8/1997 | Newman et al. .......... 424/184.1 |
| 5,858,682 A | * | 1/1999 | Gruenwald et al. ........... 435/7.1 |

FOREIGN PATENT DOCUMENTS

| | | |
|---|---|---|
| EP | 623 679 | 11/1994 |
| EP | 573 551 | 5/2003 |
| WO | WO 98/46645 | * 10/1998 |
| WO | WO 2004/106383 | 4/1999 |
| WO | WO 01/40312 | 1/2001 |
| WO | WO 01/90190 | 11/2001 |
| WO | WO 03/035694 | 5/2003 |
| WO | WO 99/54440 | 12/2004 |

OTHER PUBLICATIONS

Frenken et al, J Biotechnology 78: 11-21, 2000.*
Muyldermans et al, J Molecular Recognition 12: 131-140, 1999.*
Rudikoff et al, Proc Natl ' Acad Sci USA 79: 179, 1983.*
Kobrin et al, J Immunology 146: 2017-2020, 1991.*
Barrios et al, J Molecular Recognition 17: 332-338, 2004.*
Baynex, "Recombinant protein expression in *Escherichia coli,*" *Curr. Opin. Biotech.*, 10:411-421, 1999.
Bohlen et al, "Cytolysis of Leukemic B-cells by T-cells activated via two bispecific antibodies," *Cancer Res.*, 53:4310-4314, 1993.
Brühl, "Depletion of CCR5-expressing cells with bispecific antibodies and chemokine toxins: a new strategy in the treatment of chronic inflammatory diseases and HIV," *J. Immunol.*, 166:2420-2406, 2001.
Cortez-Retamozo et al., "Efficient tumor targeting by single-domain antibody fragments of camels," *Int. J. Cancer*, 98:456-462, 2002.
Davies and Reichmann, "Antibody VH domains as small recognition units," *Biotechnology*, 13:475-479, 1995.

Davies and Riechmann, "Single antibody domains as small recognition units: design and in vitro antigen selection of camelized, human VH domains with improved protein stability," *Protein Engineering*, 9(6):531-537, 1996.
De Jonge et al., "In vivo retargeting of T cell effector function by recombinant bispecific single chain Fv (anti-CD3×anti-idiotype) induces long-term survival in the murine BCL1 lymphoma model," *J. Immunol.*, 161:1454-1461, 1998.
Desmyter et al., "Antigen specificity and high affinity binding provided by one single loop of a camel singe-domain antibody," *J. Biol. Chem.*, 267(28):26285-26290, 2001.
Destmyter et al., "Three camelid VHH domains in complex with porcine pancreatic α-amylase," *J. Biol. Chem.*, 277(26):23645-23650, 2002.
Dumoulin et al., "Single-domain antibody fragments with high conformational stability," *Protein Science*, 11:500-515, 2002.
Conrath et al., "Camel single-domain antibodies as modular building units in bispecific and bivalent antibody constructs," *J. Biol. Chem.*, 276(10):7346-7350, 2001.
Ewert et al., "Biophysical properties of camelid VHH domains compared to those of human VH3 domains," *Biochemistry*, 41:3628-3636, 2002.
Harmsen et al., "Llama heavy-chain V regions consist of at least four distinct subfamilies revealing novel sequence features," *Molecular Immunology*, 37:579-590, 2000.
Jobling et al., "Immunomodulation of enzyme function in plants by single-domain antibody fragments," *Nature Biotech.*, 21:77-80, 2003.
Kufer et al., "Construction and biological activity of a recombinant bispecific single-chain antibody designed for therapy of minimal residual colorectal cancer," *Cancer Immunol. Immunother.*, 45:193-197, 1997.
Löffer et al., "A recombinant bispecific single-chain antibody, CD19×CD3, induces rapid and high lymphoma-directed cytotoxicity by unstimulated T lymphocytes," *Blood*, 95(6):2098-2103, 2000.
Mack et al., "Biologic properties of a bispecific single-chain antibody directed against 17-1A (EpCAM) and CD3," *J. Immunol.*, 158:3965-3970, 1997.
Mack et al., "A small bispecific antibody construct expressed as a functional single-chain molecule with high tumor cell cytotoxicity," *Proc. Natl. Acad. Sci., USA*, 92:7021-7025, 1995.
Muruganandam et al., "Selection of phage-displayed llama single-domain antibodies that transmigrate across human blood-brain barrier endothelium," *FASEB Journal*, 16:240-242, 2002.

(Continued)

*Primary Examiner*—Christina Chan
*Assistant Examiner*—Phuong Huynh
(74) *Attorney, Agent, or Firm*—Fulbright & Jaworski, LLP

(57) ABSTRACT

The present invention discloses bispecific antibodies comprising two antibody variable domains on a single polypeptide chain, wherein a first portion of the bispecific antibody is capable of recruiting the activity of a human immune effector cell by specifically binding to an effector antigen on the human immune effector cell, the first portion consisting of one antibody variable domain, and a second portion of the bispecific antibody specifically binding to a target antigen other than the effector antigen, the target antigen on a target cell other than the human immune effector cell, the second portion comprising one antibody variable domain.

2 Claims, 1 Drawing Sheet

OTHER PUBLICATIONS

Muyldermans et al., "Recognition of antigens by single-domain antibody fragments: the superfluous luxury of paired domains," *Trends in Biochemical Sciences*, 26(4):230-235, 2001.

Riechmann, "Rearrangement of the former VL interface in the solution structure of a camelised, single antibody VH domain," *J. Mol. Biol.*, 259:957-969, 1996.

Spinelli et al., "Camelid heavy-chain variable domains provide efficient combining sites to haptens," *Biochemistry*, 39:1217-1222, 2000.

Tanha et al., "Optimal design features of camelized human single-domain antibody libraries," *J. Biol. Chem.*, 276(27):24774-24780, 2001.

Borrebaeck et al., "Kinetic analysis of recombinant antibody-antigen interactions: relation between structural domains and antigen binding," *Biotechnology* (N Y), 10(6):697-8, 1992.

Ewert et al., "Biophysical properties of human antibody variable domains," *J Mol Biol*, 325:531-53, 2003.

* cited by examiner

SEQUENCE LISTING

<160> NUMBER OF SEQ ID NOS: 1

<210> SEQ ID NO 1
<211> LENGTH: 378
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 1

```
Glu Leu Val Met Thr Gln Ser Pro Ser Ser Leu Thr Val Thr Ala Gly
 1               5                  10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Gly Gly Gly Gly Ser Gly Gly Gly Gly Ser Gly Gly Gly Gly Ser
        115                 120                 125

Glu Val Gln Leu Leu Glu Gln Ser Gly Ala Glu Leu Val Arg Pro Gly
    130                 135                 140

Thr Ser Val Lys Ile Ser Cys Lys Ala Ser Gly Tyr Ala Phe Thr Asn
145                 150                 155                 160

Tyr Trp Leu Gly Trp Val Lys Gln Arg Pro Gly His Gly Leu Glu Trp
                165                 170                 175

Ile Gly Asp Ile Phe Pro Gly Ser Gly Asn Ile His Tyr Asn Glu Lys
            180                 185                 190

Phe Lys Gly Lys Ala Thr Leu Thr Ala Asp Lys Ser Ser Thr Ala
        195                 200                 205

Tyr Met Gln Leu Ser Ser Leu Thr Phe Glu Asp Ser Ala Val Tyr Phe
    210                 215                 220

Cys Ala Arg Leu Arg Asn Trp Asp Glu Pro Met Asp Tyr Trp Gly Gln
225                 230                 235                 240

Gly Thr Thr Val Thr Val Ser Ser Gly Gly Gly Ser Asp Ile Lys
                245                 250                 255

Leu Gln Gln Ser Gly Ala Glu Leu Ala Arg Pro Gly Ala Ser Val Lys
            260                 265                 270

Met Ser Cys Lys Thr Ser Gly Tyr Thr Phe Thr Arg Tyr Thr Met His
        275                 280                 285

Trp Val Lys Gln Arg Pro Gly Gln Gly Leu Glu Trp Ile Gly Tyr Ile
    290                 295                 300

Asn Pro Ser Arg Gly Tyr Thr Asn Tyr Asn Gln Lys Phe Lys Asp Lys
305                 310                 315                 320

Ala Thr Leu Thr Thr Asp Lys Ser Ser Ser Thr Ala Tyr Met Gln Leu
                325                 330                 335
```

```
-continued

Ser Ser Leu Thr Ser Glu Asp Ser Ala Val Tyr Tyr Cys Ala Arg Tyr
            340             345                 350

Tyr Asp Asp His Tyr Cys Leu Asp Tyr Trp Gly Gln Gly Thr Thr Leu
            355             360             365

Thr Val Ser Ser His His His His His
    370             375
```

BISPECIFIC ANTIBODIES

BACKGROUND OF THE INVENTION

A. Field of the Invention

The invention relates to the field of antibodies. Specifically, the invention relates to a bispecific antibody comprising two antibody variable domains on a single polypeptide chain. The invention further relates to the use of such a bispecific antibody for the preparation of a pharmaceutical composition. The invention further relates to a method for the prevention, treatment or amelioration of a disease comprising administration of an effective amount of such a bispecific antibody. Finally, the invention relates to a kit comprising such a bispecific antibody.

B. Related Art

Unifying two antigen binding sites of different specificity into a single construct, bispecific antibodies have the ability to bring together two discreet antigens with exquisite specificity and therefore have great potential as therapeutic agents. This potential was recognized early on, leading to a number of approaches for obtaining such bispecific antibodies. Bispecific antibodies were originally made by fusing two hybridomas, each capable of producing a different immunoglobulin. The resulting hybrid-hybridoma, or quadroma, was capable of producing antibodies bearing the antigen specificity of the first parent hybridoma as well as that of the second parent hybridoma (Milstein et al. (1983), *Nature* 305:537). However, the antibodies resulting from quadromas often exhibited undesired properties due to the presence of an Fc antibody portion.

Largely due to such difficulties, attempts later focused on creating antibody constructs resulting from joining two scFv antibody fragments while omitting the Fc portion present in full immunoglobulins. Each scFv unit in such constructs was made up of one variable domain from each of the heavy (VH) and light (VL) antibody chains, joined with one another via a synthetic polypeptide linker, the latter often being genetically engineered so as to be minimally immunogenic while remaining maximally resistant to proteolysis. Respective scFv units were joined by a number of techniques including incorporation of a short (usually less than 10 amino acids) polypeptide spacer bridging the two scFv units, thereby creating a bispecific single chain antibody. The resulting bispecific single chain antibody is therefore a species containing two VH/VL pairs of different specificity on a single polypeptide chain, wherein the VH and VL domains in a respective scFv unit are separated by a polypeptide linker long enough to allow intramolecular association between these two domains, and wherein the thusly formed scFv units are contiguously tethered to one another through a polypeptide spacer kept short enough to prevent unwanted association between, for example, the VH domain of one scFv unit and the VL of the other scFv unit.

Bispecific single chain antibodies of the general form described above have the advantage that the nucleotide sequence encoding the four V-domains, two linkers and one spacer can be incorporated into a suitable host expression organism under the control of a single promoter. This increases the flexibility with which these constructs can be designed as well as the degree of experimenter control during their production.

Remarkable experimental results have been obtained using such bispecific single chain antibodies designed for the treatment of malignancies (Mack, *J. Immunol.* (1997), 158:3965–70; Mack, *PNAS* (1995), 92:7021–5; Kufer, *Cancer Immunol. Immunother.* (1997), 45:193–7; Löffler, *Blood* (2000), 95:2098–103) and non-malignant diseases (Brühl, *J. Immunol.* (2001), 166:2420–6). In such bispecific single chain antibodies, one scFv unit is capable of activating cytotoxic cells, for example cytotoxic T cells, within the immune system by specifically binding to an antigen on the cytotoxic cells, while the other scFv unit specifically binds an antigen on a malignant cell intended for destruction. In this way, such bispecific single chain antibodies have been shown to activate and redirect the immune system's cytotoxic potential to the destruction of pathological, especially malignant cells. In the absence of such a bispecific single chain antibody construct, malignant cells would otherwise proliferate uninhibited.

However, bispecific single chain antibodies must fulfil additional requirements. In order to achieve the desired activity, each scFv unit of a bispecific single chain antibody should remain properly folded, something which often proves unrealisable in conventional bacterial expression systems such as *E. coli*. The need to use less conventional, more cumbersome and more costly eukaryotic—even mammalian—expression systems often complicates the production of bispecific single chain antibodies and/or reduces the amount of product obtainable to levels lower than desired for therapeutic application.

In the event that a bispecific antibody is intended for therapeutic use, it is desirable to produce high amounts of this antibody solubly and in the desired functional form. The production of functionally active antibody becomes especially critical when producing bispecific antibodies of which one portion is able to activate and recruit the cytotoxic potential of human immune effector cells. For example, a produced antibody devoid of functional activity will not lead to the desired activation of human immune effector cells, while a bispecific antibody which is functionally active, albeit not in the desired manner, as for example may be the case when the bispecific antibody is produced in a heterogeneous form containing multiple isomers, may activate and recruit the cytotoxic potential of human immune effector cells in unforeseeable and/or unintended manners.

One example of the sort of unintended activation mentioned above is the possibility of activation of human immune effector cells to exert an effect on other human immune effector cells instead of on a target cell intended for destruction. This type of immune effector cell fratricide may jeopardize the effectiveness of a regimen of therapy depending on the activity of human immune effector cells.

However, reliable production of large amounts of functional single chain antibody, especially large amounts of functional bispecific single chain antibody, from prokaryotic expression systems such as *E. coli* is often limited, necessitating costly optimization (Baneyx (1999), *Curr. Opinions Biotechnol.* 10:411–21).

In summary, bispecific antibody constructs can be of great therapeutic use in redirecting the powerful potential of the body's own immune system to achieve the destruction of diseased cells. By the same token, however, the activation of such a powerful means of eradicating or neutralizing unwanted cells requires that this power be controlled as precisely as possible so that the cytotoxic potential of the immune system is recruited and applied only in the direction intended and no other.

Clearly, when one specific binding arm of a bispecific single chain antibody is to recruit the activity of a human immune effector cell, for example a cytotoxic T cell, there exists an especially heightened and, as yet, unmet need for bispecific single chain antibodies which overcome limitations as described above.

SUMMARY OF THE INVENTION

The present inventors have found that the above limitations can be overcome with a bispecific antibody comprising two antibody variable domains on a single polypeptide chain, wherein:
  a first portion of the bispecific antibody is capable of recruiting the activity of a human immune effector cell by specifically binding to an effector antigen located on the human immune effector cell, said first portion consisting of one antibody variable domain; and
  a second portion of the bispecific antibody is capable of specifically binding to a target antigen other than the effector antigen, said target antigen being located on a target cell other than said human immune effector cell, and said second portion comprising an antibody variable domain (first aspect of the present invention).

According to one embodiment of this first aspect of the invention, the second portion of the bispecific antibody comprises two antibody variable domains. According to another embodiment of the first aspect of the invention, the second portion of the bispecific antibody comprises one antibody variable domain.

A second aspect of the invention provides a bispecific antibody comprising two antibody variable domains on a single polypeptide chain, wherein:
  a first portion of the bispecific antibody is capable of recruiting the activity of a human immune effector cell by specifically binding to an effector antigen located on the human immune effector cell, said first portion comprising an antibody variable domain, and
  a second portion of the bispecific antibody is capable of specifically binding to a target antigen other than the effector antigen, said target antigen being located on a target cell other than said human immune effector cell, and said second portion consisting of one antibody variable domain.

According to one embodiment of the second aspect of the invention, the first portion of the bispecific antibody comprises two antibody variable domains.

In its minimal form, the total number of antibody variable regions in the bispecific antibody according to the invention is thus only two. Here, not two variable domains, but rather only one variable domain, is necessary to specifically bind to each antigen of interest. The bispecific antibody of the invention is thus approximately half the size of conventional bispecific single chain antibodies containing four antibody variable domains.

The greater simplicity in molecular design of the bispecific antibody of the invention correlates to greater possible simplicity in the host expression system used for its production in functionally active form. As such, the small size of the inventive bispecific antibody opens up avenues of production hitherto closed to conventional bispecific single chain antibodies with four antibody variable domains. For example, the bispecific antibody of the invention may be easily produced in conventional, well understood and cheap bacterial expression systems such as *E. coli* in amounts which are desired for therapeutic applications.

Increased productivity has at least two highly advantageous effects. First, larger amounts of the bispecific antibody of the invention can be produced in functional form per batch than previously possible for single chain bispecific antibodies with four antibody variable domains, allowing greater efficiency and, ultimately, economy in production. Second, a greater number of constructs in the format of the bispecific antibody of the invention may now be considered as therapeutic candidates since a low cytotoxic activity of a bispecific construct with four antibody variable domains may now be offset by higher amounts of available therapeutic agent using the bispecific antibody of the invention. The palette of possible therapeutic applications for the bispecific antibody of the invention is thereby expanded relative to that of single chain bispecific antibodies with four antibody variable domains.

At the same time, less complexity in molecular design also correlates to fewer possibilities in which undesired intermolecular association may take place. That is to say, the bispecific antibody of the invention can be produced more homogeneously than possible for single chain antibody formats with four antibody variable domains. As explained above, product heterogeneity may threaten the therapeutic prognosis and/or product safety profile which can be expected from a bispecific antibody capable of binding to an immune effector cell. Decreasing the number of antibody variable domains in the bispecific antibody of the invention decreases the number of potential partners for intermolecular association. This eliminates pathways by which intermolecular association can take place. A bispecific antibody is thus obtained which retains the intended therapeutic profile while minimizing or even abolishing formation of intermolecular association products which might mobilize the host immune response in unintended manners.

In one embodiment, when either the second or the first portion of a bispecific antibody of the invention comprises two antibody variable domains as described above, these two antibody variable domains are a VH- and VL-domain which are associated with one another. However, it is also contemplated that the two antibody variable domains comprised in either the second or the first portion may be two VH domains or two VL regions which are associated with one another. In the event that the two antibody variable domains of the first or second portion are covalently associated with one another, the two antibody variable domains may be designed as an scFv fragment, meaning that the two domains are separated from one another by a peptide linker long enough to allow intermolecular association between these two domains. The design of linkers suitable for this purpose is described in the prior art, for example in the granted patents EP 623 679 B1, U.S. Pat. No. 5,258,498, EP 573 551 B1 and U.S. Pat. No. 5,525,491.

In other words, a bispecific antibody according to this embodiment of the invention is a construct with a total of three antibody variable domains. Here, one antibody variable domain specifically binds alone, i.e., without being paired with another antibody variable domain (a) either to a human immune effector cell by specifically binding to an effector antigen on the human immune effector cell or to a target cell, while the remaining two antibody variable domains together specifically bind (b) either to the target antigen on the target cell or to a human immune effector cell by specifically binding to an effector antigen on the human immune effector cell, respectively.

The inventors have found that the presence of three antibody variable domains in the bispecific antibody entails unique advantages. Often, an scFv exhibiting the desired binding specificity for a target antigen is already known and optimized, and omitting one of its two antibody variable domains would abolish or at least attenuate its binding characteristics. Such an scFv may make up part of the bispecific antibody according to the present embodiment of the invention. Specifically, such a three-domain antibody may advantageously comprise an entire scFv as either its effector antigen- or target antigen-conferring portion.

Effectively, then, the present embodiment of the invention allows a bispecific antibody to be formed starting from a desired scFv by simple incorporation of only one additional antibody variable domain into the same polypeptide chain as the scFv, wherein the one additional antibody variable domain incorporated has an antigen binding specificity different than that of the scFv.

In this context, it has been found that such incorporation of a third antibody variable domain to form a three-domain bispecific single chain antibody according to this embodiment leads to the same, or substantially the same, production characteristics as described above for the two-domain bispecific antibodies of the invention. For example, problems such as low yield, restriction to complicated expression systems, heterogeneous products, etc., recounted above for bispecific antibodies with four antibody variable domains pose little to no problem when expressing three-domain bispecific antibodies according to this embodiment.

It would seem, then, that a bispecific antibody according to this embodiment of the invention and including no more than three antibody variable domains would represent the upper limit in number of antibody variable domains for which high yielding, homogeneous production is possible while still allowing the researcher to employ preexisting binding molecules such as scFv constructs. As such, the molecular architecture according to this embodiment allows for savings in research time and resources while still conferring the advantages associated with the bispecific antibody of the invention in its minimal form.

According to a further embodiment of the invention, the first and second portions of the bispecific antibody according to the invention or according to any of the above embodiments of the invention may be separated from one another by a synthetic polypeptide spacer moiety, which covalently (i.e., peptidically) links either the C-terminus of the first portion with the N-terminus of the second portion, or the C-terminus of the second portion with the N-terminus of the first portion. As such, the portions of the bispecific antibody according to this embodiment may be arranged, as either N-(first portion)-(second portion)-C or N-(second portion)-(first portion)-C.

The term "human immune effector cell" refers to a cell within the natural repertoire of cells in the human immune system which, when activated, is able to bring about a change in the viability of a target cell. The term "viability of a target cell" may refer within the scope of the invention to the target cell's ability to survive, proliferate and/or interact with other cells. Such interaction may be either direct, for example when the target cell contacts another cell, or indirect, for example when the target cell secretes substances which have an influence on the functioning of another distant cell. The target cell may be either native or foreign to humans. In the event that the cell is native to humans, the target cell is advantageously a cell which has undergone transformation to become a malignant cell. The native cell may additionally be a pathologically modified native cell, for example a native cell infected with an organism such as a virus, a plasmodium or a bacterium. In the event that the cell is foreign to humans, the target cell is advantageously an invading pathogen, for example an invading bacterium or plasmodium.

According to a further embodiment of the invention, the antibody variable domains of the first and/or second portions may be derived from identical or separate animal species. This has the advantage that for each portion of the bispecific antibody, optimal antibody variable domain/s can be chosen to be derived from the animal species known to yield the best antibodies against a particular effector and/or target antigen. In this way, this embodiment allows the researcher to capitalize on already known, developed and/or optimized specificities such that the efficiency of workflow in developing bispecific antibodies as described herein is maximized.

In one preferred embodiment, the first and/or second portion of the bispecific antibody are/is independently derived from an antibody produced in primate, rodent, tylopoda or cartilaginous fish.

The first and/or second portion of a bispecific antibody according to this embodiment may be either naturally occurring or genetically engineered. Alternatively, it is within the scope of the present embodiment that part of a naturally occurring antibody is used as a substrate on which further genetic engineering is performed, to finally yield a derivative of the naturally occurring part of the antibody for use in the first or second portion of a bispecific antibody according to this embodiment.

In the event that the first and/or second portion of the bispecific antibody are/is derived from rodent, said first and/or second portion may advantageously be derived independently from mouse or rat antibodies. In this way, one seeking to develop and/or optimize bispecific antibodies according to this embodiment of the invention can benefit from the preexisting and highly diverse palette of known murine and rat antibody sequences which bind relevant human antigens.

In the event that a primate antibody is used as a basis for the first and/or second portion of the bispecific antibody, said first and/or second portion are/is advantageously derived independently from human antibodies. Besides benefiting from the ever-growing diversity of known human antibodies, use of human antibody variable domains entails the further advantage that the resulting bispecific antibodies will elicit little to no immunogenic response when administered as part of a therapeutic regimen in human patients. Such bispecific antibodies are thus especially suitable as therapeutic agents for use in humans.

In the event that a tylopoda-derived antibody variable domain is used in the first and/or second portion of a bispecific antibody according to this embodiment of the invention, said first and/or second portion may advantageously be derived independently from camel, llama or/and dromedary. This use of such "camelid" antibodies allows the researcher seeking to develop or optimize bispecific antibodies according to this embodiment of the invention to capitalize on the unique types of antibodies known to be produced by these species. These species are namely known to produce high affinity antibodies of only a single variable domain. In the event that a tylopoda antibody is used as the source for the antibody variable domain in the first and/or second portion of the bispecific antibody, it is advantageous to use the VHH domain or a modified variant thereof.

The term "VHH" denotes a variable region of a heavy chain of a so-called "camelid" antibody. Camelid antibodies comprise a heavy chain, but lack a light chain. As such, a VHH region from such a camelid antibody represents the minimal structural element required to specifically bind to an antigen of interest in these species. Camelid VHH domains have been found to bind to antigen with high affinity (Desmyter et al. (2001), *J. Biol. Chem.* 276:26285–90) and possess high stability in solution (Ewert et al. (2002), *Biochemistry* 41:3628–36).

In the event that said first and/or second portion of the bispecific antibody is derived from a cartilaginous fish, said cartilaginous fish is advantageously a shark.

In the event that a rodent or primate antibody is used as the source for the antibody variable domain in the first and/or second portion of a bispecific antibody according to this embodiment of the invention, it is advantageous to use the VH domain or a modified variant thereof. The VH domain of antibodies in these species is known to contribute significantly to the binding specificity and affinity observed for a given antibody. At an absolute minimum, it is advantageous to use at least the third complementarity determining region (CDR) from a VH domain of such a parent antibody in designing the first and/or second portion of the bispecific antibody. This is due to the fact that the VH-CDR3 is known to play a major role in the specificity and affinity of binding of all the CDR regions, of which there are three in each of VH and VL.

According to a further embodiment of the invention, the bispecific antibody may be subjected to an alteration to render it less immunogenic when administered to a human. Such an alteration may comprise one or more of the techniques commonly known as chimerization, humanization, CDR-grafting, deimmunization and/or mutation of framework region amino acids to correspond to the closest human germline sequence (germlining). Subjecting the bispecific antibody of the invention to such an alteration/s has the advantage that a bispecific antibody which would otherwise elicit a host immune response is rendered more, or completely "invisible" to the host immune system, so that such an immune response does not occur or is reduced. Bispecific antibodies which have been altered as described according to this embodiment will therefore remain administrable for a longer period of time with reduced or no immune response-related side effects than corresponding bispecific antibodies which have not undergone any such alteration(s). One of ordinary skill in the art will understand how to determine whether, and to what degree an antibody must be altered in order to prevent it from eliciting an unwanted host immune response.

According to another embodiment of the invention, the human immune effector cell is a member of the human lymphoid cell lineage. In this embodiment, the effector cell may advantageously be a human T cell, a human B cell or a human natural killer (NK) cell. Advantageously, such cells will have either a cytotoxic or an apoptotic effect on the target cell. Especially advantageously, the human lymphoid cell is a cytotoxic T cell which, when activated, exerts a cytotoxic effect on the target cell. According to this embodiment, then, the recruited activity of the human effector cell is this cell's cytotoxic activity.

According to a preferred embodiment, activation of the cytotoxic T cell may occur via binding of the CD3 antigen as effector antigen on the surface of the cytotoxic T cell by a bispecific antibody of this embodiment of the invention. The human CD3 antigen is present on both helper T cells and cytotoxic T cells. Human CD3 denotes an antigen which is expressed on T cells as part of the multimolecular T cell complex and which comprises three different chains: CD3-epsilon, CD3-delta and CD3-gamma.

The activation of the cytotoxic potential of T cells is a complex phenomenon which requires the interplay of multiple proteins. The Tcell receptor ("TCR") protein is a membrane bound disulfide-linked heterodimer consisting of two different glycoprotein subunits. The TCR recognizes and binds foreign peptidic antigen which itself has been bound by a member of the highly diverse class of major histocompatibility complex ("MHC") proteins and has been presented, bound to the MHC, on the surface of antigen presenting cells ("APCs").

Although the variable TCR binds foreign antigen as outlined above, signaling to the T cell that this binding has taken place depends on the presence of other, invariant, signaling proteins associated with the TCR. These signaling proteins in associated form are collectively referred to as the CD3 complex, here collectively referred to as the CD3 antigen.

The activation of T cell cytotoxicity, then, normally depends first on the binding of the TCR with an MHC protein, itself bound to foreign antigen, located on a separate cell. Only when this initial TCR-MHC binding has taken place can the CD3-dependent signaling cascade responsible for T cell clonal expansion and, ultimately, T cell cytotoxicity ensue.

However, binding of the human CD3 antigen by the first or second portion of a bispecific antibody of the invention activates T cells to exert a cytotoxic effect on other cells in the absence of independent TCR-MHC binding. This means that T cells may be cytotoxically activated in a clonally independent fashion, i.e., in a manner which is independent of the specific TCR clone carried by the T cell. This allows an activation of the entire T cell compartment rather than only specific T cells of a certain clonal identity.

In light of the foregoing discussion, then, an especially preferred embodiment of the invention provides a bispecific antibody in which the effector antigen is the human CD3 antigen. The bispecific antibody according to this embodiment of the invention may have a total of either two or three antibody variable domains.

According to further embodiments of the invention, other lymphoid cell-associated effector antigens bound by a bispecific antibody of the invention may be the human CD16 antigen, the human NKG2D antigen, the human NKp46 antigen, the human CD2 antigen, the human CD28 antigen or the human CD25 antigen.

According to another embodiment of the invention, the human effector cell is a member of the human myeloid lineage. Advantageously, the effector cell may be a human monocyte, a human neutrophilic granulocyte or a human dendritic cell. Advantageously, such cells will have either a cytotoxic or an apoptotic effect on the target cell. Advantageous antigens within this embodiment which may be bound by a bispecific antibody of the invention may be the human CD64 antigen or the human CD89 antigen.

According to another embodiment of the invention, the target antigen is an antigen which is uniquely expressed on a target cell in a disease condition, but which remains either non-expressed, expressed at a low level or non-accessible in a healthy condition. Examples of such target antigens which might be specifically bound by a bispecific antibody of the invention may advantageously be selected from EpCAM, CCR5, CD19, HER-2 neu, HER-3, HER-4, EGFR, PSMA, CEA, MUC-1 (mucin), MUC2, MUC3, MUC4, MUC5$_{AC}$, MUC5$_B$, MUC7, βhCG, Lewis-Y, CD20, CD33, CD30, ganglioside GD3, 9-O-Acetyl-GD3, GM2, Globo H, fucosyl GM1, Poly SA, GD2, Carboanhydrase IX (MN/CA IX), CD44v6, Sonic Hedgehog (Shh), Wue-1, Plasma Cell Antigen, (membrane-bound) IgE, Melanoma Chondroitin Sulfate Proteoglycan (MCSP), CCR8, TNF-alpha precursor, STEAP, mesothelin, A33 Antigen, Prostate Stem Cell Antigen (PSCA), Ly-6; desmoglein 4, E-cadherin neoepitope, Fetal Acetylcholine Receptor, CD25, CA19-9 marker, CA-125 marker and Muellerian Inhibitory Substance (MIS) Receptor type II, sTn (sialylated Tn antigen; TAG-72), FAP (fibroblast activation antigen), endosialin, EGFRvIII, LG, SAS and CD63.

According to a specific embodiment, the target antigen specifically bound by a bispecific antibody may be a cancer-related antigen, that is an antigen related to a malignant condition. Such an antigen is either expressed or accessible on a malignant cell, whereas the antigen is either not present, not significantly present, or is not accessible on a non-malignant cell. As such, a bispecific antibody according to this embodiment of the invention is a bispecific antibody which recruits the activity of a human immune effector cell against the malignant target cell bearing the target antigen, or rendering the target antigen accessible.

In a particular embodiment of the invention, the bispecific antibody specifically binds to the human CD3 antigen as effector antigen and to the human CD19 antigen as target antigen. The human CD19 antigen is expressed in the whole human B lineage from the pro B cell to the mature B cell, it is not shed, is uniformly expressed on all lymphoma cells, and is absent from stem cells. Thus, a bispecific antibody according to this embodiment, namely one which specifically binds to the human CD3 antigen as effector antigen and to the human CD19 antigen as target antigen, is of great potential value as a therapeutic for the eradication of malignant B cells. A bispecific antibody according to this embodiment consists of two or three antibody variable domains, separated by spacer and possibly linker polypeptides as described above.

In a further particular embodiment of the invention, the bispecific antibody specifically binds to the human CD3 antigen as effector antigen and to the human EpCAM antigen as target antigen. EpCAM ("Epithelial cell adhesion molecule", also called 17-1A antigen, KSA, EGP40, GA733-2, ks1-4 or esa) is a 40 kDa membrane integrated glycoprotein of 314 amino acids with specific expression in certain epithelia and on many human carcinomas. EpCAM has been shown in various studies to be beneficial in diagnosis and therapy of various carcinomas. Furthermore, in many cases, tumor cells were observed to express EpCAM to a much higher degree than their parental epithelium or less aggressive forms of said cancers. Thus, a bispecific antibody according to this embodiment, namely one which specifically binds to the human CD3 antigen as effector antigen and to the human EpCAM antigen as target antigen is of great potential value as a therapeutic for the eradication of malignant epithelial cells. A bispecific antibody according to this embodiment consists of two or three antibody variable domains, separated by spacer and possibly linker polypeptides as described above.

An anti-CD3×anti-EpCAM bispecific antibody according to this latter embodiment may advantageously have the amino acid sequence as set out in SEQ ID NO: 1. A bispecific antibody according to this embodiment has as its first portion a murine-derived VH specifically binding the human CD3 antigen as effector antigen and, as its second portion, an scFv unit specifically binding the human EpCAM antigen as target antigen. As such, SEQ ID NO: 1 represents a bispecific antibody with three antibody variable domains. The advantages of this type of construct are described hereinabove.

A further aspect of the invention provides a use of a bispecific antibody as disclosed hereinabove for the preparation of a pharmaceutical composition for the prevention, treatment or amelioration of a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease.

A further aspect of the invention provides a method for the prevention, treatment or amelioration a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease in a subject in the need thereof, said method comprising the step of administration of an effective amount of a bispecific antibody as disclosed hereinabove.

According to a preferred embodiment, the prevention, treatment or amelioration occurs in a human. The tumorous disease is preferably selected from the group of B cell disorders, for example a lymphoma, a B cell lymphoma and a Hodgkin's lymphoma. In a further embodiment, the B cell lymphoma is a non-Hodgkin's lymphoma. In a further embodiment, the autoimmune disease is selected from rheumatoid arthritis, multiple sclerosis, type 1 diabetes mellitus, inflammatory bowel disease, systemic lupus erythematosus, psoriasis, scleroderma and autoimmune thyroid diseases.

According to a further embodiment, any administration of a bispecific antibody as described hereinabove may advantageously be coupled with the administration of a proteinaceous compound capable of providing an activation signal for immune effector cells. Such a proteinaceous compound may advantageously be administered simultaneously or non-simultaneously with the bispecific antibody.

A further aspect of the invention is a kit comprising a bispecific antibody as disclosed hereinabove.

Throughout the instant application, it is to be understood that use of a term in the singular may imply, where appropriate, use of the respective term in the plural. Similarly, use of a term in the plural may imply, where appropriate, use of the respective term in the singular.

BRIEF DESCRIPTION OF THE DRAWING

The following drawings form part of the present specification and are included to further demonstrate certain aspects of the present invention. The invention may be better understood by reference to one or more of these drawings in combination with the detailed description of specific embodiments presented herein.

EXAMPLES

Example 1

Figure 1:
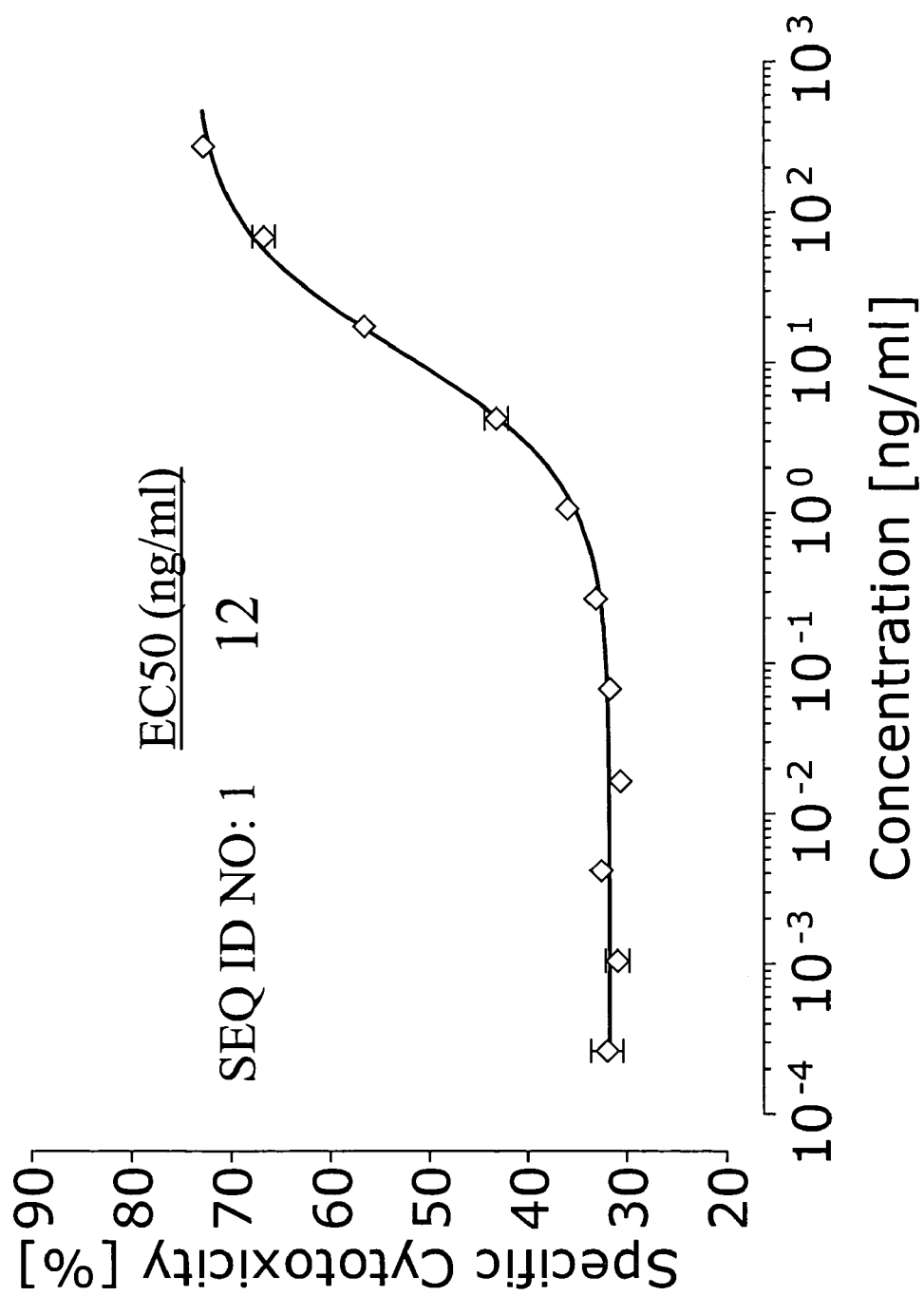
FIG. 1—Cytotoxic activity of an anti-EpCAM×anti-CD3 antibody comprising three variable domains

Design, Prokaryotic Expression and Purification of a Bispecific Antibody With Three Antibody Variable Domains The DNA encoding an anti-EpCAM×anti-CD3 bispecific antibody with a VL and VH in the anti-EpCAM portion of the molecule and only one antibody variable domain (VH) in the anti CD3 portion of the molecule are cloned in the multiple cloning site (MCS) of pET-20b(+) vector (Novagen). The expression of the bispecific antibody with a Histidine (×6) tag is induced with IPTG. The choice of the vector facilitates the transport of the recombinant proteins into the periplasm. Other cloning vectors such as pBAD-gIII (Invitrogen), pET-32 series (+) vector (Novagen) may also be used. For pBAD-gIII-based expression, arabinose is used to induce recombinant gene expression instead of IPTG. In any case it is important to ensure that the DNA encoding the bispecific antibody is cloned in-frame with the sequence encoding the signal peptide (e.g., PeIB, OmpA) that mediates the transport of the recombinant protein into the periplasm.

The pET-20b (+) containing the DNA encoding the anti-EpCAM×anti-CD3 bispecific antibody described above is cloned and propagated in the bacterial host strain DH5. The recombinant bispecific antibody is expressed using the BL21 (DE3) bacterial host strain (Novagen). Alternatively, the Rosetta (DE3) bacterial host strain (Novagen) works when using a pET vector as described above. Alternatively, the pBAD-gIII vector may be used with the TOP10 E. coli strain (Invitrogen).

A single colony of host cell transformed with the vector pET-20b(+) containing DNA encoding the anti-EpCAM× anti-CD3 bispecific antibody described above is selected and inoculated into 50 ml LB containing the essential antibiotics. Cells are grown and harvested according to the supplier's instruction manual. The culture is incubated at 37° C. until an OD600 of 0.4 to 1.0 is reached (0.6 is an ideal value), followed by induction of expression by addition of appropriate amounts of IPTG. The incubation is continued for an additional 2–3 h.

Cultures as described are harvested by centrifugation. The cell pellet is suspended in 30 ml of 30 mM Tris-HCl pH 8, 20% sucrose. To this suspension, 60 µl of EDTA (0.5 M, pH 8) is added to a final concentration of 1 mM. The cells are collected by centrifugation and the cell-pellet is subjected to shock by re-suspending the pellet thoroughly for 10 min in the cold with chilled $MgSO_4$ (5 mM, 30 ml) solution. The shocked cells are subjected to centrifugation in order to separate the periplasmic (supernatant) and cellular (pellet) fractions. The supernatant is then further analysed by SDS-PAGE and is also checked for activity.

Bispecific antibody produced as described above with a His tag is purified using a Ni—NTA spin column kit (Qiagen, catalog no. 31314) following the protocol provided in the Qiagen instruction manual. Alternatively, the Ni—NTA magnetic agarose beads (Qiagen, catalog no. 36113) can also be used.

The polypeptide thus purified may be described as bispecific antibody with three antibody variable domains located on the same polypeptide chain. Progressing from the amino- to carboxy terminus, the bispecific single chain antibody contains the following elements: anti-human EpCAM VL; 15 amino acid linker of sequence $(Gly_4Ser)_3$; anti-human EpCAM VH; 5 amino acid spacer of sequence $Gly_4Ser$; anti-human CD3 VH; $His_6$. The sequence is as set out in SEQ ID NO: 1.

Example 2

Cytotoxicity Assay

The ability of the bispecific antibody with the sequence set out in SEQ ID NO: 1 to recruit the cytotoxic potential of human cytotoxic T cells to effect the killing of cells bearing the human EpCAM antigen was measured in a cytotoxicity assay as follows.

CHO cells from the American Type Cell Culture Collection (ATCC, USA) were transfected to express, human epithelial cell adhesion molecule (EpCAM) as the target antigen. Cells cultured from the resulting cell clone, referred to as CHO-EpCAM cells, were subsequently used in the cytotoxicity experiments as the target cells. The human cell line MC15 was used as a source of effector cells bearing the effector antigen CD3. The cell clone was derived from the cell clone CB15, which is a CD4-positive human T cell clone kindly provided by Dr. Fickenscher at the University of Erlangen/Nürnberg, Germany. Cells were cultured as recommended by the respective suppliers.

$1.5 \times 10^7$ target cells were washed twice with phosphate-buffered saline (PBS) and were labeled with PKH26 dye (Sigma-Aldrich Co.) according to the manufacturer's instructions. After staining, the cells were washed two times with 20 ml of PBS. Labeled CHO-EpCAM cells (target cells) and MC15 cells (effector cells) were mixed together in a ratio of 1:5, respectively. The resulting cell suspension contained 400,000 target and $2 \times 10^6$ effector cells per ml. BiTEs were diluted to different concentrations in alpha MEM/10% FCS-medium.

Typically, each reaction (of volume 100 µl) contained a mixture of 20,000 target cells, $1 \times 10^5$ effector cells and a specific concentration of the bispecific antibody set out as in SEQ ID NO: 1. Measurements at each concentration of bispecific antibody were performed in triplicate. Reactions were incubated for about 20 h at 37° C./5% $CO_2$.

Propidium iodide was added to a final concentration of 1 µg/ml. Propidium iodide stains dead cells. The reaction samples were analyzed by flow cytometry (e.g., FACS-Calibur Becton Dickinson). The population of PKH26-labeled target cells was gated in an FSC versus FL-2 plot and subsequent analysis of cells was carried out only with the cell population identified within this gate. The percent of dead cells (propidium iodide stained) was determined in an FSC (forward scatter) versus FL-3 plot. Mean values were plotted against concentrations of bispecific antibody on a logarithmic scale, resulting in a typical dose response curve (see FIG. 1). The $EC_{50}$ (the concentration of bispecific antibody required to elicit a half-maximal cytotoxic response) values were obtained after non-linear fitting of the data obtained with the GraphPad Prism software.

As can be seen in FIG. 1, the bispecific antibody with the sequence as set out in SEQ ID NO: 1 showed activity as a recruiter of cytotoxic T cells. This follows from the fact that the target cells are efficiently killed (with an $EC_{50}$ value of about 12 ng/ml) in a manner depending on the concentration of bispecific antibody added to a respective reaction mixture in the presence of cytotoxic T cells.

All of the methods and compositions disclosed and claimed herein can be made and executed without undue experimentation in light of the present disclosure. While the compositions and methods of this invention have been described in terms of preferred embodiments, it will be apparent to those of skill in the art that variations may be applied to the methods and compositions and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A bispecific antibody comprising three antibody variable domains on a single polypeptide chain, wherein:
- a first portion of the bispecific antibody is capable of recruiting the activity of a human immune effector cell by specifically binding to an effector antigen located on the human immune effector cell, said first portion consisting of one antibody variable domain; and
- a second portion of the bispecific antibody is capable of specifically binding to a target antigen other than the effector antigen, said target antigen being located on a target cell other than said human immune effector cell, and said second portion comprising two antibody variable domains, wherein the effector antigen is the human CD3 antigen, the target antigen is the human EpCAM antigen, and the bispecific antibody has a sequence as set forth in SEQ ID NO:1.

2. A kit comprising the bispecific antibody of claim 1.

* * * * *